United States Patent
Faz

[19]

[11] Patent Number: 6,065,659

[45] Date of Patent: May 23, 2000

[54] HOLDER FOR I.V. CATHETERS AND RELATED MEDICAL ARTICLES

[76] Inventor: Ray J. Faz, 2228 Riverview Dr., Grand Island, Nebr. 68801

[21] Appl. No.: 09/203,615

[22] Filed: Dec. 1, 1998

[51] Int. Cl.[7] ............................................. A45F 5/00
[52] U.S. Cl. ................... 224/661; 224/223; 224/250; 224/269; 224/684; 206/570; 206/803
[58] Field of Search ................................ 224/223, 194, 224/575, 586, 660, 661, 666, 250, 269, 676, 681, 682, 684; 383/39; 206/803, 570, 370, 373

[56] References Cited

U.S. PATENT DOCUMENTS

| | | | |
|---|---|---|---|
| 1,094,009 | 4/1914 | Parkhurst | 206/373 |
| 3,134,416 | 5/1964 | Magyar | 383/39 X |
| 4,169,550 | 10/1979 | Williams | 206/803 X |
| 4,682,691 | 7/1987 | Spiering | 206/373 |
| 4,688,572 | 8/1987 | Hubbard et al. | 224/222 X |
| 4,728,037 | 3/1988 | Mainhardt | 224/194 X |
| 4,796,790 | 1/1989 | Hamilton | 206/803 X |
| 4,967,986 | 11/1990 | Schildkraut | 224/250 |
| 5,573,154 | 11/1996 | Tietze | 224/586 X |
| 5,833,093 | 11/1998 | Honaker et al. | 224/269 X |

FOREIGN PATENT DOCUMENTS

| | | | |
|---|---|---|---|
| 387 | of 1902 | United Kingdom | 206/373 |
| 607133 | 8/1948 | United Kingdom | 190/103 |
| 92/11832 | 7/1992 | WIPO | 206/570 |

*Primary Examiner*—Gregory M. Vidovich
*Attorney, Agent, or Firm*—Zarley, McKee, Thomte, Voorhees & Sease; Dennis L. Thomte

[57] ABSTRACT

A holder for I.V. catheters and related medical articles during storage and use is disclosed comprising a generally rectangular flexible sheet member having an elastic strap extending from one end thereof which may be extended around the rolled-up holder to maintain the holder in that condition. The inner surface of the sheet member is provided with a plurality of pockets for storing I.V. catheters, alcohol wipes, tourniquets, etc. A pair of elastic straps are secured to one end of the sheet member at the inner surface thereof for use as tourniquets. A pocket is also provided at one end of the sheet member for receiving a sharps container therein. A clip is secured to the strap member extending from end of the sheet member for securing the holder to a belt or other clothing item of a paramedic.

12 Claims, 3 Drawing Sheets

HOLDER FOR I.V. CATHETERS AND RELATED MEDICAL ARTICLES

BACKGROUND OF THE INVENTION

1. Field of the Invention

This invention relates to a holder for I.V. catheters and related medical articles and more particularly to a holder for I.V. catheters and related medical articles during storage and use.

2. Description of the Related Art

Medical personnel, such as paramedics, travel to locations where they are needed by way of ambulance. The paramedics normally store medical supplies, such as I.V. catheters, tourniquets, tape, sharps containers, etc., in a tray or box in the ambulance. Normally, many different types of catheters are stored in the tray in the ambulance, with each of those catheters being individually contained within a package. Catheters of a particular size are normally separated from other catheters by means of a rubber band or the like being extended around groups of catheters. During a medical emergency, the storage tray or the like is removed from the ambulance and taken to the scene where the medical supplies are needed. If the storage tray becomes upset during use, the medical supplies are scattered, which is inconvenient and possibly dangerous. Further, there are times when the paramedic needs to have the medical supplies within easy reach and it is not possible for the storage tray to be positioned within each reach of the paramedic. The fact that the various groups of catheters are wrapped with a rubber band or the like makes it inconvenient for one of the catheters to be removed from the group of catheters. Further, the packaging for the catheters may become damaged during storage which results in the catheter becoming contaminated.

SUMMARY OF THE INVENTION

A holder for I.V. catheters and related medical articles during storage and use is described and is comprised of an elongated, generally rectangular, flexible sheet member adapted to be rolled up for storage. The flexible sheet member has an inner face, an outer face, an upper edge, a lower edge, and first and second ends. First and second elongated strips of elastic material are secured to the inner face between the lower upper edges with the first and second strips being secured to the inner face at spaced-apart positions along their lengths to define aligned pockets which are adapted to receive and display I.V. catheters therein. Other elastic strips are secured to the inner face of the sheet member for storing other items therein. A pair of elastic strap members are secured to the sheet member adjacent its first end which may be used as a tourniquet. The second end of the sheet member is provided with a pocket adapted to have a sharps container therein to enable needles to be inserted therein. An alligator-type clip is secured to the elastic strap member at the outer face thereof so that the holder may be secured to the paramedic's person in either a rolled-up condition or in an unrolled condition. When the holder is secured to the paramedic's person by the alligator-type clip in an unrolled condition, a pair of strap members which are secured to the second end of the sheet member may be wrapped around the paramedic's leg to keep the holder closely positioned against the paramedic's leg.

A principal object of the invention is to provide a holder for I.V. catheters.

Still another object of the invention is to provide a holder for I.V. catheters and related medical articles during storage and use.

Still another object of the invention is to provide a holder for I.V. catheters and related medical articles wherein the catheters are positioned in pockets formed on the inner surface of the holder.

Still another object of the invention is to provide a holder of the type described which includes a pocket for a sharps container.

Still another object of the invention is to provide a holder for I.V. catheters and related medical articles during storage and use with means for maintaining the holder in a rolled-up condition.

Still another object of the invention is to provide a holder of the type described which may be secured to the clothing of a paramedic or the like by means of an alligator-type clip so that the holder is within convenient reach of the paramedic.

Still another object of the invention is to provide a holder for I.V. catheters and related medical articles which prevents the catheters from becoming damaged during storage.

Still another object of the invention is to provide a holder for I.V. catheters and related medical articles having means for holding the I.V. catheters therein in a manner which conveniently displays the catheters after the holder has been unrolled.

These and other objects will be obvious to those skilled in the art.

DESCRIPTION OF THE PREFERRED EMBODIMENT

Figure 1:
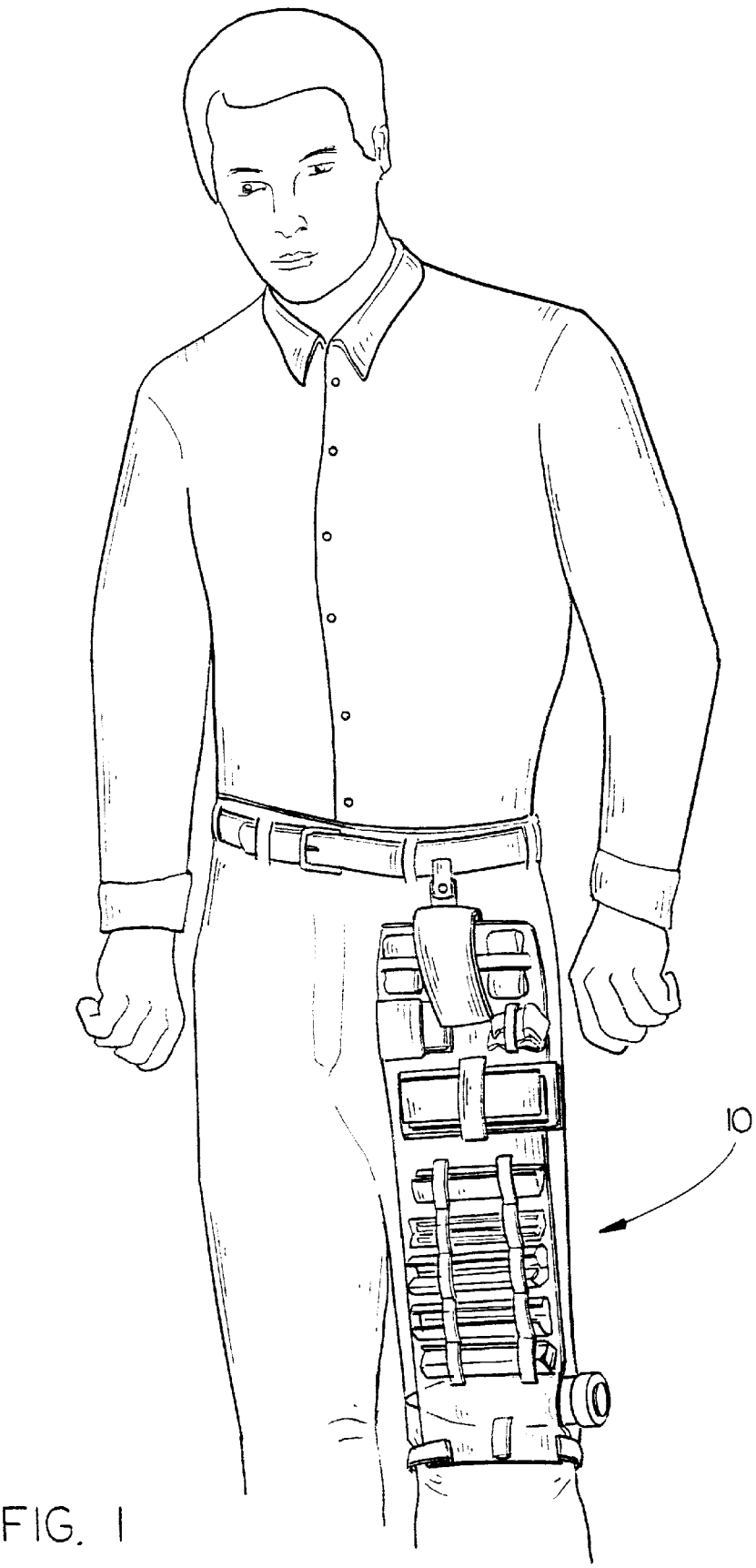
FIG. 1 is a perspective view illustrating the holder of this invention secured to a person's belt and being unrolled therefrom and secured to the leg of the person.
Figure 2:
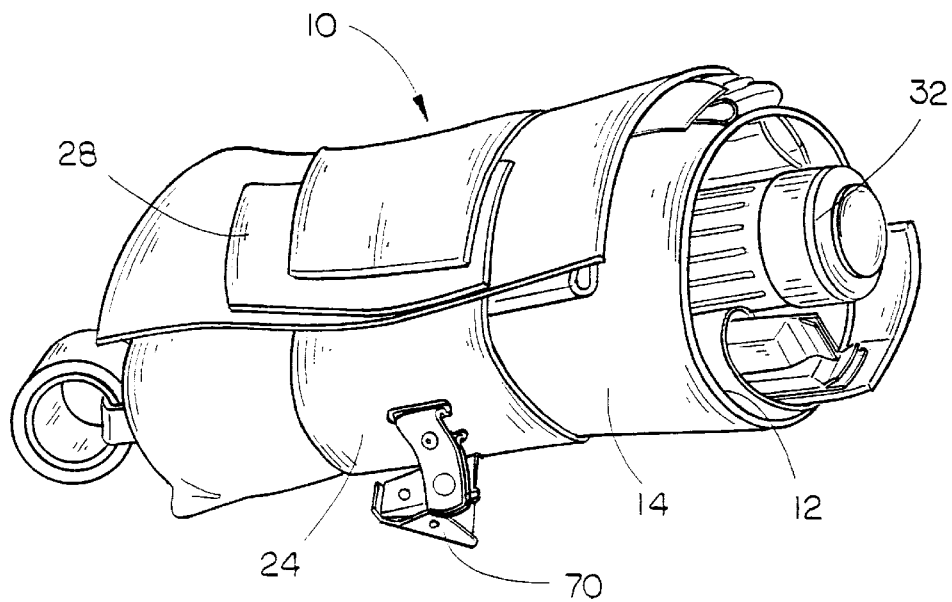
FIG. 2 is a perspective view of the holder of this invention in a rolled-up condition.
Figure 3:
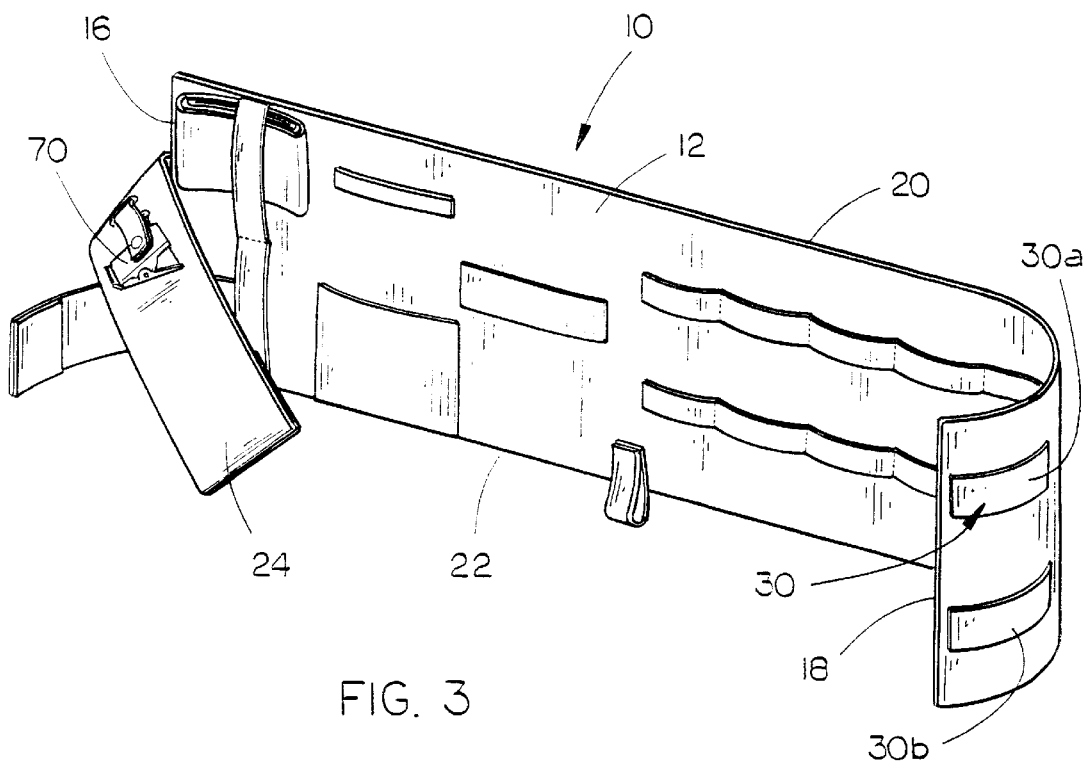
FIG. 3 is a perspective view of the holder of this invention in an unrolled condition.
Figure 4:
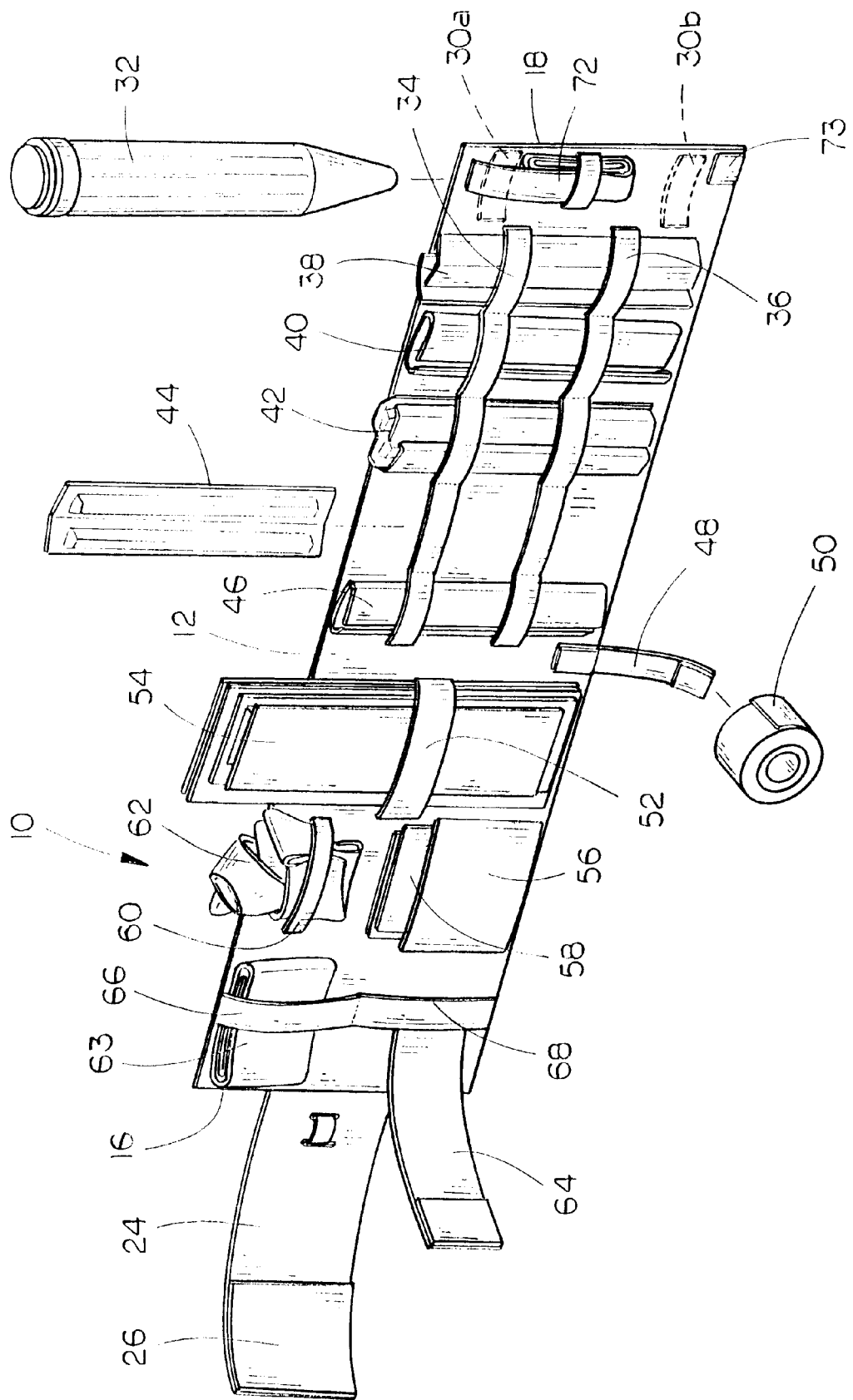
FIG. 4 is a perspective view illustrating the holder in an unrolled position and various medical articles positioned therein.

The holder for I.V. catheters and related medical articles during storage and use is referred to generally by the reference numeral 10. Holder 10 is constructed of a flexible material which has a generally rectangular shape including an inner surface 12, outer surface 14, ends 16 and 18, upper edge 20 and bottom edge 22. A flexible elastic strap 24 is secured to end 16 of holder 10 and extends therefrom, as seen in the drawings. The inner surface of strap 24 has Velcro™ loop fasteners 26 on its inner surface which are adapted to be secured to the Velcro™ hook fasteners 28 secured to the outer surface 14 of holder 10 adjacent end 16 so that the holder may be rolled-up and held in the rolled-up position by means of the strap 24, as seen in the drawings.

Holder 10 includes a pocket 30, formed by elastic straps 30a and 30b, adjacent end 18 adapted to receive a sharps container 32 therein. Elongated elastic strip members 34 and 36 are secured to the inner surface 12 of holder 10 and are stitched to the inner surface 12 at predetermined spaced-apart positions to define aligned pockets therein which are adapted to receive groups of catheters 38, 40, 42, 44 and 46 therein. Normally, the catheters contained in each of the pockets will have a different size. As seen, the catheters are well-displayed when the holder is in its unrolled condition.

An elastic strap 48 is secured at one end to holder 10 adjacent bottom edge 22, as seen in the drawings. Strap 48 has Velcro™ fasteners associated therewith so that the strap may be formed into a loop and secured upon itself to support a tape roll 50 therein.

The ends of an elastic strap 52 are also secured to inner surface 12 of holder 10 to form a pocket which is adapted to receive medical supplies 54 such as dressing and sponges therein. An elastic member 56 is also stitched to the inner surface 12 of holder 10 at three of its sides to define an open upper end adapted to receive packages of alcohol wipes or the like referred to generally by the reference numeral 58. The opposite ends of an elastic strap 60 are secured to inner surface 12 of holder 10 to form a pocket adapted to receive a tourniquet 62 therein with the tourniquet being in a folded or rolled condition. A pair of elastic straps 63 and 64 are also secured, at one end thereof, to inner surface 12 of holder 10 adjacent end 16 and are normally held in a folded condition by the elastic strips or straps 66 and 68, respectively. The straps 63 and 64 may be removed from beneath the straps 66 and 68, respectively, and used as a tourniquet.

An alligator-type clip 70 is secured to the outer surface of strap 24 and is designed to a be attached to support such as the belt or other clothing item of the paramedic so that the holder may be supported on the paramedic in a convenient manner whether the holder 10 is in its rolled-up condition or its unrolled condition. When the holder 10 is secured to a clothing item of the paramedic and is in its unrolled condition, as seen in FIG. 1, the elastic strap 72 which is secured to holder 10 adjacent end 18 may be extended around the paramedic's leg and held in place by the Velcro™ fasteners on the ends of the strap 72 in engagement with the Velcro™ fastener 73 on holder 10 so that the holder will be closely positioned adjacent the paramedic's leg within easy reach of the paramedic.

Thus it can be seen that a novel holder has been provided for I.V. catheters and related medical articles during storage and use. The holder, when its rolled-up condition, protects the catheters and the other medical articles therein from becoming damaged. The holder is convenient to use and eliminates most of the disadvantages associated with storage trays or the like.

Thus it can be seen that the invention accomplishes at least all of its stated objectives.

I claim:

1. A holder for I.V. catheters and related medical articles during storage and use, comprising:

an elongated, generally rectangular, flexible sheet member adapted to be rolled up and having an inner face, an outer face, an upper edge, a lower edge, and first and second ends;

a first elongated strip of elastic material secured to said inner face below said upper edge and being substantially parallel thereto;

a second elongated strip of elastic material secured to said inner face above said lower edge and being substantially parallel thereto;

said first and second strips being secured to said inner face at spaced-apart positions along their lengths to define aligned pockets which are adapted to receive and display I.V. catheters therein;

said sheet member adapted to be rolled up whereby said first end of said sheet member is positioned within the rolled up holder and wherein said second end of said sheet member is positioned at the outside of the holder;

means for maintaining the holder in its rolled up condition comprising a first strip of a loop fastener material secured to said outer face of said sheet member at said second end, an elongated elastic strap member secured to said second end of said sheet member and extending outwardly therefrom, said strap member having inner and outer faces, said inner face having a hook material secured to its inner face for attachment to said loop fastener material; and an attachment clip being secured to said strap member at the outer face thereof whereby said holder is clippable onto a support.

2. The holder of claim 1 wherein first and second tourniquet straps are secured to said inner face of said sheet member at one of said first and second ends thereof for use as a tourniquet.

3. The holder of claim 2 wherein each of said tourniquet straps is comprised of an elongated, elastic material.

4. The holder of claim 3 further including means for storing said tourniquet straps in a folded stored position.

5. The holder of claim 1 wherein said flexible sheet member has means at its said outer face adjacent said first end for removably receiving a sharps container therein.

6. The holder of claim 5 wherein said means for removably receiving a sharps container comprises a pair of elongated, spaced-apart elastic members having their longitudinal axes disposed parallel to the length of said flexible sheet member.

7. The holder of claim 1 wherein said inner face of said sheet member has an elastic pocket positioned thereon for supporting alcohol prep packages therein.

8. The holder of claim 1 wherein said inner face of said sheet member has an elastic pocket thereon for supporting dressings and sponges therein.

9. The holder of claim 1 wherein said sheet member has an elastic strap member secured thereto for supporting a roll of tape.

10. The holder of claim 1 wherein said inner face of said sheet member has a pocket comprising an elastic strap member secured to said inner face for receiving a tourniquet therein.

11. The holder of claim 1 wherein a retaining strap, having opposite ends, is secured at one of its ends to said inner face of said sheet member at said first end of said sheet member and has a loop fastener material at its other end, said inner face of said sheet member having a hook fastener material positioned thereon for receiving the loop fastener material on said retaining strap to enable said retaining strap to be extended around the person's leg when the holder is unrolled and hereby said holder is supported by said attachment clip from a person's clothing.

12. The holder of claim 11 further including means on said inner face of said sheet member for maintaining said retaining strap member in a folded stored position.

* * * * *